United States Patent
Nikaido

[11] Patent Number: 6,015,698
[45] Date of Patent: Jan. 18, 2000

[54] METHOD OF PRODUCING D-AMINO ACID AND METHOD OF PRODUCING AMINE

[75] Inventor: Teruyuki Nikaido, Tsukuba, Japan

[73] Assignee: Daicel Chemical Industries, Ltd., Sakai, Japan

[21] Appl. No.: 09/023,884

[22] Filed: Feb. 13, 1998

[51] Int. Cl.$^7$ .............................. C12P 13/04; C12P 13/22
[52] U.S. Cl. ........................ 435/106; 435/108; 435/232; 435/280
[58] Field of Search .................................. 435/106, 108, 435/280, 232

[56] References Cited

U.S. PATENT DOCUMENTS

| | | | |
|---|---|---|---|
| 3,930,948 | 1/1976 | Sano et al. ............................... | 435/232 |
| 4,497,957 | 2/1985 | Nakai et al. ............................. | 548/496 |
| 5,552,318 | 9/1996 | Houng et al. ........................... | 435/280 |
| 5,728,555 | 3/1998 | Fotheringham et al. ................ | 435/106 |
| 5,814,520 | 9/1998 | De Luca et al. ........................ | 435/419 |

FOREIGN PATENT DOCUMENTS

| | | |
|---|---|---|
| 61-234780 | 10/1986 | Japan . |
| 7-24587 | 3/1995 | Japan . |

OTHER PUBLICATIONS

M. Ferencik, et al., "Amino Acid Decarboxylases in Some Fungi", Amino Acid Decarboxylases in Fungi, 1968, Folia Microbiology 13, pp. 414–418.

*Primary Examiner*—Herbert J. Lilling
*Attorney, Agent, or Firm*—Fish & Richardson P.C.

[57] ABSTRACT

D-amino acid with high optical purity represented by formula (1-A) and/or formula (1-B),

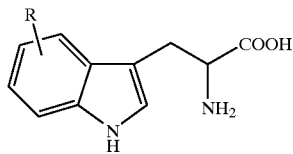
(1-A)

wherein R represents H or OH,

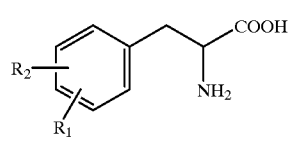
(1-B)

wherein $R_1$, $R_2$ each represents H or OH, and amine represented by formula (2-A) and/or formula (2-B)

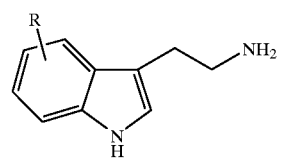

(2-A)

wherein R represents H or OH,

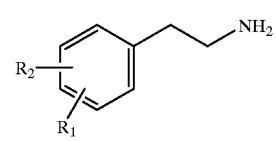
(2-B)

wherein $R_1$ and $R_2$ each represents H or OH, can be produced economically in an industrial scale by contacting a mixture of enantiomers of amino acid represented by the above formula (1-A) and/or formula (1-B) with a microorganism capable of selectively degrading L-amino acid or with at least one of the treated products of the microorganism.

16 Claims, No Drawings

METHOD OF PRODUCING D-AMINO ACID AND METHOD OF PRODUCING AMINE

FIELD OF THE INVENTION

The present invention relates to a method of producing D-amino acid, which is important as a starting material for drugs, particularly for antibiotics, using a microorganism, and to a method of producing amine belonging to biologically active amines, which are important as drugs, using a microorganism.

BACKGROUND OF THE INVENTION

As biochemical methods for production of aromatic D-amino Acid, a known method comprises contacting DL-allylmethylhydantoin with a microorganism capable of selectively hydrolyzing D-allylmethylhydantoin to N-carbamoyl-D-amino acid to synthesize N-carbamoyl-D-amino acid and hydrolyzing N-carbamoyl-D-amino acid to D-amino acid chemically, for example, with nitrous acid, or using a microorganism to produce D-amino acid (hydantoinase method, JP-A-Sho 61-17791).

It is also known to produce D-amino acid by a method comprising contacting DL-amino acid amide with a microorganism or enzyme capable of selectively hydrolyzing D-amino acid amide alone in DL-amino acid amide (D-amidase method, JP-B-Hei 08-22228) and a method comprising selectively hydrolyzing L-amino acid amide alone in DL-amino acid amide and chemically hydrolyzing the remaining D-amino acid amide (L-amidase method, JP-A-Sho 57-13000).

Further, other known methods of producing D-amino acid include a method comprising contacting indole pyruvic acid, phenyl pyruvic acid, and the like and D-alanine as an amino group donor with D-amino acid transaminase (transaminase method, JP-B-Hei 07-85718), a method comprising contacting N-acetyl-DL-amino acid with L-aminoacylase capable of selectively deacetylating N-acetyl-L-amino acid and chemically deacetylating remaining N-acetyl-D-amino acid (L-aminoacylase method, Methods in Enzymology 3, 554–570 (1957)), a method comprising contacting N-acetyl-D-amino acid with D-aminoacylase capable of selectively deacetylating N-acetyl-DL-amino acid (D-aminoacylase method, JP-B-Hei 01-29560), and a method comprising contacting DL-amino acid with D-amino acid acetyltransferase to selectively convert D-amino acid to N-acetyl-D-amino acid and, after separation from the remaining L-amino acids, chemically hydrolyzing N-acetyl-D-amino acid thus formed (acetyltransferase method, JP-A-Sho 60-251892).

On the other hand, as methods for biochemical production of aromatic amine, there have been reported a method comprising decarboxylation of L-tyrosine using tyrosine decarboxylase derived from microorganism belonging to the genus Streptococcus to obtain tyramine (JP-A-Sho 55-102393), a similar method to the above by which dopamine is obtained from L-dopa (JP-A-Sho 55-102394), a method of producing amine from the corresponding amino acid using aromatic amino acid decarboxylase derived from the genus Micrococcus belonging to bacteria (Nakazawa, H. et al., Biosci. Biotechnol. Biochem. 57(7), 1210–1211 (1993)), and a method of obtaining amine from the corresponding aromatic amino acid using a microorganism belonging to the genus Staphylococcus (JP-A-Sho 50-155689).

Aromatic amino acid decarboxylases are known to be distributed among mammals, insects, plants, and microorganisms. However, regarding those derived from microorganisms, only aromatic amino acid decarboxylase derived from microorganisms belonging to the genus Micrococcus (Nakazawa, H. et al., Biosci. Biotechnol. Biochem. 57(7), 1210–1211(1993)), aromatic amino acid decarboxylase derived from *Pholiota nameko* (JP-A-Sho 61-234780), and microorganisms belonging to the genus Staphylococcus (JP-A-Sho 50-155689) have been reported to have aromatic amino acid decarboxylating activity. At present, there is no report that fungi belonging to the genera Fusarium, Gibberella, Aspergillus, Pleurotus, Nectria, and the like have aromatic amino acid decarboxylase. There is also no report of production of aromatic D-amino acid and corresponding amine from a mixture of enantiomers of aromatic amino acid using microorganisms belonging to these genera. Some microorganisms belonging to the genus Fusarium are reported to have phenylalanine decarboxylase activity (Ferencik M. and Ladzianska K., Folia Microbiology 13, 414–418 (1968)). This report describes that the amino acid decarboxylation reaction was limitedly carried out within pH 4.6–5.6 and that the microorganisms did not act on tryptophan and tyrosine. Further, there is no description in this report of the use of microorganism for selective degradation of L-amino acid to produce D-amino acid.

Thus, concerning the microorganisms belonging to the genera Fusarium, Gibberella, Aspergillus, Pleurotus, Nectria, it has not been reported so far that various aromatic amino acids, especially the L-form thereof, are selectively decarboxylated to form the corresponding amines and that selective degradation of L-amino acid results in a remarkable increase in the content of D-amino acid in the reaction system.

Further, the above-described conventional methods have drawbacks for industrial production of aromatic D-amino acid and amine because the substrates are expensive, the reaction steps are complicated, the yield is low, and the optical purity of the product is low.

SUMMARY OF THE INVENTION

An object of the present invention is to provide an industrially bearable method of producing D-amino acid and amine. Specifically, the present invention aims at providing a method of producing D-amino acid and amine using a microorganism capable of selectively degrading L-amino acid.

In view of the drawbacks of the conventional methods as described above, the present inventors investigated ardently paying special attention to easiness for synthesis of substrates, economic performance, and stereoselective decarboxylation reaction by the action of enzymes. As a result, the present inventors have found that microorganisms belonging to the genera Fusarium, Gibberella, Aspergillus, Pleurotus, and Nectria characteristically act on amino acids represented by formula (1-A) or formula (1-B), which can be easily synthesized, to produce amines represented by formula (2-A) or formula (2-B). It has been also found that the microorganisms have property to selectively degrade only L-form amino acids represented by formula (1-A) or formula (1-B) in the amine-producing reaction and, as a result, the content of D-form amino acids present in the reaction system is increased remarkably. Furthermore, the present inventors have found that amine and D-amino acid can be simply and easily separated and purified from each other by usual method from a mixture thereof obtained using the above microorganisms. Thus, it has been found that the separation and purification method enables production of D-amino acid with optically high purity in high yield.

The present invention relates to an industrially bearable method of producing D-amino acid and amine, particularly to a method of producing D-amino acid and amine using microorganisms. More specifically, the present invention relates to (1) a method of producing D-amino acid which comprises contacting a mixture of enantiomers of amino acid represented by formula (1-A) and/or formula (1-B)

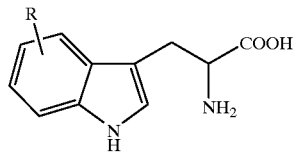

(1-A)

wherein R represents H or OH,

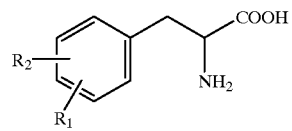

(1-B)

wherein $R_1$ and $R_2$ each represents H or OH, with microorganisms capable of producing amine represented by formula (2-A) and/or formula (2-B)

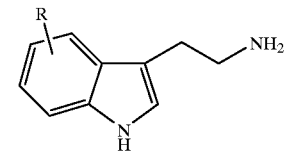

(2-A)

wherein R represents H or OH,

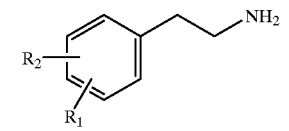

(2-B)

wherein $R_1$ and $R_2$ each represents H or OH, by selective degradation of L-amino acid in the amino acid represented by formula (1-A) and/or formula (1-B) or with at least a kind of treated products of the microorganisms and recovering the remaining D-amino acid. Preferably, (2) the method as described in (1) above in which the microorganisms belong to the genus selected from the group consisting of Fusarium, Gibberella, Aspergillus, Pleurotus, and Nectria. More preferably, (3) the method as described in (1) above in which the microorganisms belong to the species selected from the group consisting of *Fusarium oxysporum, Fusarium solani, Gibberella fujikuroi, Aspergillus oryzae, Aspergillus candidus, Pleurotus ostreatus,* and *Nectria flammea*, and more preferably, (4) the method as described in (1) above in which the microorganisms are selected from the group consisting of *Fusarium oxysporum* IFO 30705, IFO 31630, *Fusarium solani* IFO 9975, *Gibberella fujikuroi* IFO 9977, IFO 30336, IFO 30337, IFO 31251, NRIC 1240, *Aspergillus oryzae* IFO 5375, IFO 4265, JCM 2059, *Aspergillus candidus* IFO 4309, IFO 8816, *Pleurotus ostreatus* IFO 6515, and *Nectria flammea* IFO 9628, and IFO 30306.

The present invention also relates to (5) a method of producing amine represented by formula (2-A) and/or formula (2-B) which comprises contacting a mixture of enantiomers of amino acid represented by formula (1-A) and/or formula (1-B) or optically pure L-amino acid represented by formula (1-A) and/or formula (1-B) with microorganisms capable of producing amine represented by formula (2-A) and/or formula (2-B) through selective degradation of L-amino acid in the amino acid represented by formula (1-A) and/or formula (1-B) or with at least a kind of treated products of the microorganisms, preferably to, (6) the method as described in (5) above in which the microorganisms belong to the genus selected from the group consisting of Fusarium, Gibberella, Aspergillus, Pleurotus, and Nectria, more preferably to, (7) the method as described in (5) above in which the microorganisms belong to the species selected from the group consisting of *Fusarium oxysporum,, Fusarium solani, Gibberella fujikuroi, Aspergillus oryzae, Aspergillus candidus, Pleurotus ostreatus,* and *Nectria flammea,* and particularly preferably to, (8) the method as described in (5) above in which the microorganisms are selected from the group consisting of *Fusarium oxysporum* IFO 30705, IFO 31630, *Fusarium solani* IFO 9975, *Gibberella fujikuroi* IFO 9977, IFO 30336, IFO 30337, IFO 31251, NRIC 1240, *Aspergillus oryzae* IFO 5375, IFO 4265, JCM 2059, *Aspergillus candidus* IFO 4309, IFO 8816, *Pleurotus ostreatus* IFO 6515, and *Nectria flammea* IFO 9628, IFO 30306.

DETAILED DESCRIPTION OF THE INVENTION

Any microorganism can be used as long as they are capable of selectively degrading L-amino acid of amino acid represented by formula (1-A) and/or formula (1-B) and producing amine represented by formula (2-A) and/or formula (2-B). It is preferable to use the microorganisms belonging to the genera Fusarium, Gibberella, Aspergillus, Pleurotus, and Nectria. More preferable microorganisms are those belonging to the species selected from the group consisting of *Fusarium oxysporum, Fusarium solani, Gibberella fujikuroi, Aspergillus oryzae, Aspergillus candidus, Pleurotus ostreatus,* and *Nectria flammea*. Still more preferably are those selected from the group consisting of *Fusarium oxysporum* IFO 30705, IFO 31630, *Fusarium solani* IFO 9975, *Gibberella fujikuroi* IFO 9977, IFO 30336, IFO 30337, IFO 31251, NRIC 1240, *Aspergillus oryzae* IFO 5375, IFO 4265, JCM2059, *Aspergillus candidus* IFO 4309, IFO 8816, *Pleurotus ostreatus* IFO 6515, and *Nectria flammea* IFO 9628, IFO 30306. For example, microorganisms belonging to the genus Fusarium used in the present invention are capable of acting on amino acid represented by formula (1-A) in addition to amino acid represented by formula (1-B) and selectively degrade L-amino acid contained therein to produce corresponding amine. Accordingly, it is possible not only to produce amine represented by formula (2-A) and/or formula (2-B) by contacting a mixture of enantiomers of amino acid represented by formula (1-A)

and/or formula (1-B) with the microorganisms belonging to the genus Fusarium used in the present invention, but also to produce D-form of amino acid by recovering the remaining D-form amino acid. It is also possible to produce amine represented by formula (2-A) and/or formula (2-B) by contacting optically pure L-amino acid represented formula (1-A) and/or formula (1-B) with the microorganisms. As such microorganisms, any strain can be suitably used, including wild strains, variants, or recombinant strains produced by genetic techniques such as cell fusion or gene manipulation. The treated products of the above-mentioned microorganisms can also be used in the present invention. The term "treated products" used herein means all the fractions showing activity of the above-mentioned microorganisms which are treated, for example, by disruption, with acetone or toluene, or by lyophilization.

Microorganisms with the "IFO" number are described in the 10th edition of Microorganism Catalogue published by Institute for Fermentation, Osaka (1996) and can be obtained from the institute, while those with the "JCM" number are described in the 6th edition of the Bacterial Strain Catalogue published by the Institute of Physical and Chemical Research (1995) and can be obtained from the institute. Microorganisms with the "NRIC" number are described in the 2nd edition of the Bacterial Strain Catalogue published by the Tokyo Agricultural University (1992) and can be obtained from the university.

According to the above-mentioned "10th edition of Microorganism Catalogue, pp.362 (1996)" published by Institute for Fermentation, Osaka and the "Handbook of Microorganisms, the 1st volume pp.518–522, the second volume pp.1055–1059, Kodansha Publishing (1978)", the conidiospore stage of *Gibberella fujikuroi* is called *Fusarium moniliforme* and, thus, the perfect stages of these microorganisms and the conidiopore stages corresponding to each perfect stage are considered as the same species of organisms.

The culture medium used for culturing the microorganisms to be used in this invention are not particularly limited as long as the microorganism can proliferate therein. Any carbon source, which is usable by the above-mentioned microorganisms, can be used. Examples thereof include sugars such as glucose, fructose, sucrose, and dextrin, alcohol such as sorbitol and glycerol, organic acids such as fumaric acid, citric acid, acetic acid, and propionic acid and the salts thereof, hydrocarbons such as paraffin, and mixtures of these materials. Examples of nitrogen sources include ammonium salts of inorganic acids such as ammonium chloride, ammonium sulfate, and ammonium phosphate, ammonium salts of organic acids such as ammonium fumarate, and ammonium citrate, meat extract, yeast extract, corn steep liquor, hydrolysate of casein, inorganic and organic nitrogen-containing compounds such as urea, and mixtures of these materials. In addition, nutrients that are used for ordinary culture such as organic salts, trace mineral salts, and vitamins may be mixed as needed. Further, it is possible to add factors that promote the proliferation of the microorganisms, factors that can enhance productivity of the desired compounds of the present invention, such as amino acid inducers, e.g., serine, tyrosine, valine, leucine, alanine, isoleucine, glycine, phenylalanine, and tryptophan, and vitamin $B_6$s, e.g., pyridoxal-5'-phosphate and pyridoxal hydrochloride, and the substances like $CaCO_3$ that are effective to keep a pH value of the culture media, if necessary. For example, YM culture medium and potato-sucrose medium are appropriate for culturing fungi (cf. the 10th edition of the Microorganisms Catalogue published by Institute for Fermentation, Osaka (1996), pp 498–500).

Culturing can be carried out anaerobically or aerobically in the culture medium at the pH of usually 3.0–11.0, preferably 4.0–8.0, and at the temperature of usually 20–45° C., preferably 25–37° C., for usually about 5–120 hours, preferably about 24–96 hours, under conditions suitable for growth of the microorganisms used.

The mixture of enantiomers of amino acid of formula (1-A) and/or formula (1-B) and L-amino acid of formula (1-A) and/or formula (1-B) to be used as substrates are added either at a time or intermittently, or continuously, to a concentration of usually about 0.01–20% (w/w). Substrates may be added in the form of a solution or dispersion in water, a solution in a organic solvent that do not affect the reaction, or a dispersion in a surfactant or the like.

Microorganisms can be used in a state of the culture medium, as cells separated from the culture medium by centrifugation or the like, or cells resuspended in buffer, water, or the like after they are separated by centrifugation and washed. It is possible to start the reaction by adding the mixture of enantiomers of amino acid of formula (1-A) and/or formula (1-B), and L-amino acid of formula (1-A) and/or formula (1-B) to microorganisms in the above-described state. Microbial cells can be used in a state as they are recovered, as their disrupts, as treated with acetone or toluene, or as lyophilizate. Microbial cells can also be used after immobilization with carageenan gel, alginate gel, polyacrylamide gel, cellulose, or agar using a known method. The cells may be reacted in a reaction vessel using a ultrafilteration membrane. To facilitate the permeability of the amino acid enantiomer mixture used as substrate into the microbial cells, surfactants such as cetyl pyridinium chloride, cetyl trimethylammonium bromide, Triton X, and Tween may be added to a concentration of approximately 0.001–0.5%, which sometimes achieves favorable results. Oxygen may be blocked by replacement of the gas phase in the reaction system with nitrogen or sealing of the liquid surface with liquid paraffin, which also sometimes leads to good results. The reaction temperature ranges usually from 5 to 70° C., preferably from 25–60° C. The pH during the reaction may be set within the range that enzymes catalyzing decarboxylation can react and is usually 5–10, preferably 6–9. The reaction is carried out in a buffer or using a pH-stat. The reaction may be carried out at a static state, or with shaking or stirring. Water is usually used as a solvent for the reaction, but an organic solvent such as alcohol may be added to an extent not to affect the reaction. Amine produced and remaining D-amino acid can be recovered and purified by an appropriate combination of the usual methods including ultrafiltration, concentration, column chromatography, extraction, and crystallization.

The present invention provides the industrially bearable method of producing D-amino acid and amine. According to the present invention, a mixture of enantiomers of amino acid represented by formula (1-A) and/or formula (1-B) can be decarboxylated stereoselectively to easily obtain amine represented by formula (2-A) and/or formula (2-B) by using a microorganism belonging to the genus Fusarium, Gibberella, Aspergillus, Pleurotus, or Nectria or the treated products thereof. At the same time, it is possible to selectively degrade L-amino acid in a mixture of enantiomers of amino acid represented by formula (1-A) and/or formula (1-B) to increase the content of D-amino acid, thereby obtaining D-amino acid with high optical purity.

The following Examples further illustrate the present invention in detail, but are not construed to limit the scope of the invention.

In the following Examples, optical purity of the remaining amino acid was measured by HPLC using "CROWNPAK CR(+)" (Daicel Chemical Industries, Ltd.) (column: CROWNPAK CR(+)(Ø4.6×150 mm), mobile phase: perchloric acid solution (pH 2.0), temperature: 10° C., flow rate: 1.0 ml/min, detection: UV 220 nm).

The amino acids used as substrates and amines produced were determined by reverse phase HPLC using ODS column (column: Wakosil ODS II HG (Ø4.6×250 mm), flow rate: 1.0 ml/min, detection: 254 nm). In this occasion, the mobile phase and the reaction temperature were set depending on the substrates as follows. In the case of tryptophan and phenylalanine, conditions used were: "mobile phase: 50 mM potassium phosphate buffer, pH 2.5/acetonitrile (9:1, v/v), temperature: 50° C.", in the case of 5-hydroxytryptophan: "mobile phase: 50 mM potassium phosphate buffer (pH 2.5), temperature: 45° C.", and in the case of tyrosine and DOPA (3,4-dihydroxyphenylalanine): "mobile phase: 50 mM potassium phosphate buffer (pH 2.5), temperature: 20° C.".

"Culture medium for preparation of microbial cells 1" and "YM medium" used in the following Examples are prepared as follows. For "Culture medium for preparation of microbial cells 1", 24 g of glucose, 19.2 g of yeast extract (Asahi Breweries, Ltd.), 2.4 g of $(NH_4)_2SO_4$, 1.3 g of $MgSO_4.7H_2O$, and 0.3 g of FS antifoam 028 (Dow Corning Co.) were mixed and deionized water was added thereto to make the total volume to 1000 ml followed by adjusting the pH to 6.0. For "YM medium", 10 g of glucose, 3 g of yeast extract (Kyokuto Seiyaku Co.), 3 g of malt extract (Kyokuto Seiyaku Co.), and 5 g of polypeptone (Nihon Seiyaku Co.) were mixed and deionized water was added thereto to make the total volume to 1000 ml followed by adjusting the pH to 6.0.

The term "DL-" used in the following Examples means racemates.

EXAMPLE 1

Production of tryptamine by *Gibberella fujikuroi*

Five ml each of the culture medium for preparation of microbial cells 1 was poured to test tubes having an internal diameter of 21 mm. After sterilization, the medium was inoculated by a loopful of *Gibberella fujikuroi* IFO 9977, IFO 30336, IFO 30337, IFO 31251, and NRIC 1240 and cultured with shaking for 72 hours at 30° C. A 2.0 ml portion of the culture medium was taken out, 0.1 ml of a 5% solution of Tween 80 was added thereto, and the medium was incubated at 30° C. for 15 min. Microbial cells obtained by subjecting the culture medium to centrifugation were washed twice with McIlvaine buffer (0.2M $Na_2HPO_4$, 0.1M citric acid, pH 6.2) and were suspended in the buffer to make 1.0 ml. The suspension was put into the test tubes having an internal diameter of 15 mm followed by addition of 1.0 ml of 2% DL-tryptophan/0.4 mM pyridoxal-5'-phosphate suspension (in McIlvaine buffer (pH 6.2)). Then, 2.0 ml of liquid paraffin was superimposed thereon and the suspension was allowed to stand for 17 hours at 30° C. to carry out the reaction. After completion of the reaction, the aqueous phase was taken out and centrifuged to obtain supernatant, which was subjected to HPLC to determine the amount of produced tryptamine. The results are shown in Table 1.

TABLE 1

| Strain | Amount produced (mM) | Yield (%) |
| --- | --- | --- |
| Gibberella fujikuroi IFO 9977 | 5.2 | 10.6 |
| Gibberella fujikuroi IFO 30336 | 10.4 | 21.3 |
| Gibberella fujikuroi IFO 30337 | 6.3 | 12.9 |
| Gibberella fujikuroi IFO 31251 | 2.3 | 4.7 |
| Gibberella fujikuroi NRIC 1240 | 3.2 | 6.5 |

EXAMPLE 2

Production of tryptamine by *Fusarium oxysporum*, etc.

A loopful of each strain of *Fusarium oxysporum* IFO 30705, IFO 31630, *Fusarium solani* IFO 9975, *Aspergillus oryzae* IFO 5375, IFO 4265, JCM 2059, *Aspergillus candidus* IFO 4309, IFO 8816, *Pleurotus ostreatus* IFO 6515, and *Nectria flammea* IFO 9628, IFO 30306 was inoculated to 5 ml of the culture medium for preparation of microbial cells 1 and shake culture was carried out for 72 hours at 30° C. in the same manner as in Example 1. A 2.0 ml portion of the culture medium was taken out, 0.1 ml of a 5% solution of Tween 80 was added thereto, and the culture medium was incubated at 30° C. for 15 min. Microbial cells obtained by centrifugation were washed twice with 100 mM Tris-HCl buffer (pH 8.0) and were suspended in the same buffer to make 1.0 ml. The suspension was put into the test tubes having an internal diameter of 15 mm followed by addition of 1.0 ml of 4% DL-tryptophan/0.4 mM pyridoxal-5'-phosphate buffer (in 100 mM Tris-HCl buffer (pH 8.0)). Then, 2.0 ml of liquid paraffin was superimposed thereon and the suspension was allowed to stand at 30° C. for 17 hours. After completion of the reaction, the aqueous phase was taken out and the supernatant was obtained by centrifugation. Produced tryptamine in the supernatant was determined by HPLC. The results were shown in Table 2.

TABLE 2

| Strain | Amount produced (mM) | Yield (%) |
| --- | --- | --- |
| Fusarium Oxysporum IFO 30705 | 2.75 | 2.8 |
| Fusarium Oxysporum IFO 31630 | 9.70 | 9.9 |
| Fusarium solani IFO 9975 | 4.11 | 4.2 |
| Asperqillus oryzae IFO 5375 | 0.60 | 0.6 |
| Asperqillus oryzae IFO 4265 | 0.70 | 0.7 |
| Aspergillus oryzae JCM 2059 | 2.57 | 2.6 |
| Aspergillus candidus IFO 4309 | 0.28 | 0.3 |
| Aspergillus candidus IFO 8816 | 0.29 | 0.3 |
| Pleurotus ostreatus IFO 6515 | 0.50 | 0.5 |
| Nectria flammea IFO 9628 | 1.4 | 1.4 |
| Nectria flammea IFO 30306 | 2.6 | 2.7 |

EXAMPLE 3

Production of D-tryptophan and tryptamine by *Fusarium solani* IFO 9975

The culture medium for preparation of microbial cells 1 (600 ml) was placed in a 1.2 L minijar (Marubishi Bioengi Co.) and sterilized at 121° C. for 15 min. After cooling, 6 ml of the culture of *Fusarium solani* IFO 9975 that had been shake-cultured in YM medium (5 ml/Ø21 mm test tube) at 30° C. for 24 hours was inoculated thereinto and cultured at 30° C., 600 rpm, and 1.0 vvm for 72 hours. The culture medium (100 ml) was centrifuged, washed twice with 50 ml of 100 mM Tris-HCl buffer, pH 8.0, and suspended in the same buffer to make 100 ml. Two g of crystals of DL-tryptophan and 2 ml of 10 mM pyridoxal-5'-phosphate solution were added thereto followed by stirring with a magnetic stirrer as needed to carry out the reaction at 30° C.

for 48 hours. HPLC analysis of the reaction mixture revealed the production of 7.6 g/l of tryptamine (yield: 48%). The concentration of the remaining tryptophan was 10.2 g/l. Its optical purity was determined by HPLC and was found to be 95% e.e. D-form.

EXAMPLE 4

Production of various amines by *Fusarium solani* IFO 9975

To 2.0 ml of the culture medium prepared in Example 3 were added 0.1 ml of a 5% Tween 80 solution. The resulting mixture was incubated at 30° C. for 15 min. Microbial cells obtained by centrifugation were washed twice with 100 mM Tris-HCl buffer (pH 8.0) and was suspended in the same buffer to make 4.0 ml. A 1.0 ml portion of the suspension was each put into 4 test tubes having an internal diameter of 15 mm. To the respective test tubes was added 1.0 ml of a solution or a suspension of (1) 50 mM DL-tryptophan, (2) 50 mM DL-phenylalanine, (3) 25 mM L-tyrosine, or (4) 50 mM DL-5-hydroxytryptophan (each containing 0.4 mM pyridoxal-5'-phosphate in 100 mM Tris-HCl buffer (pH 8.0)). Then, 2.0 ml of liquid paraffin was superimposed thereon and the suspension was allowed to stand at 30° C. for 17 hours to carry out the reaction. Separately, the same reaction as above was carried out for the microbial cells prepared using 100 mM borax-$KH_2PO_4$ buffer, pH 8.0, as the buffer after the treatment with Tween 80, to which (5) 25 mM L-DOPA solution/0.4 mM pyridoxal-5'-phosphate (in 100 mM borax- $KH_2PO_4$ buffer, pH 8.0) was added. After completion of the reaction, the aqueous phase was taken out and the supernatant was obtained by centrifugation. Amines produced in the supernatants corresponding to each starting amino acid were determined by HPLC. The results are shown in Table 3.

TABLE 3

| Substrates | Amine concentration (mM) | Relative activity (%) |
|---|---|---|
| DL-tryptophan | 14.7 | 100 |
| DL-phenylalanine | 19.1 | 130 |
| L-tyrosine | 25.2 | 171 |
| DL-5-hydroxytryptophan | 0.3 | 2.0 |
| L-DOPA | 2.1 | 14.3 |

EXAMPLE 5

Production of D-tryptophan and tryptamine by *Fusarium oxysporum* IFO 31630

*Fusarium oxysporum* IFO 31630 was cultured in the same manner as in Example 3 to prepare live microbial cells except for changing the culturing period to 48 hours. Further, the microbial cells were reacted with DL-tryptophan under the same conditions as in Example 3. After 48-hour reaction, the reaction mixture was analyzed by HPLC, resulting in the production of 6.9 g/l of tryptamine (yield of 44%). The concentration of the remaining tryptophan was 10.8/l and its optical purity determined by HPLC was D-form 81% e.e.

EXAMPLE 6

Production of various amines by *Fusarium oxysporum* IFO 31630

Using the microbial cells prepared in Example 5, the reaction was carried out in the same manner as in Example 4. The results are shown in Table 4.

TABLE 4

| Substrates | Amine concentration (mM) | Relative activity (%) |
|---|---|---|
| DL-tryptophan | 1.92 | 100 |
| DL-phenylalanine | 5.86 | 305 |
| L-tyrosine | 2.48 | 129 |
| DL-5-hydroxytryptophan | 0.11 | 6 |
| L-DOPA | 0.74 | 39 |

EXAMPLE 7

Production of D-tryptophan and tryptamine by *Gibberella fujikuroi* IFO 30337

The culture medium for preparation of microbial cells 1 (600 ml) was placed into a 1.2 L minijar (Marubishi Bioengi Co) and sterilized at 121° C. for 15 min. After cooling, 6 ml of the culture of *Gibberella fujikuroi* IFO 30337, which had been shake-cultured in YM medium (25 ml/Sakaguchi (shouldered) flask) for 24 hours at 30° C., was inoculated in the above minijar and cultured at 30° C., at 900 rpm, and at 1.0 vvm for 72 hours. The total amount of the culture medium was centrifuged, washed twice with the same volume of deionized water, and suspended in deionized water to a volume of 200 ml to make a cell suspension. Two hundred ml of the cell suspension was added to the reaction mixture prepared by adding 388 ml of deionized water, 6 g of crystals of DL-tryptophan and 12 ml of 10 mM pyridoxal-5'-phosphate to the above-mentioned minijar and stirring the mixture. Then, the mixture was allowed to react at 40° C., at 200 rpm for 44 hours with slightly introducing nitrogen gas. The pH during the reaction was adjusted to 6.2 with 10% $H_2SO_4$. After completion of the reaction, the reaction mixture was analyzed by HPLC and, as a result, 3.8 g/l of tryptamine and 4.7 g/l of tryptophan were found to remain. The optical purity of D-tryptophan was not less than 99% e.e. and the yield of the compounds was 48% and 47%, respectively.

EXAMPLE 8

Production of various amines by *Gibberella fujikuroi* IFO 30337

To 10.0 ml of the culture medium prepared in Example 7 was added 0.5 ml of a 5% Tween 80 solution. The resulting mixture was incubated at 30° C. for 15 min and centrifuged to obtain live microbial cells, which were washed twice with McIlvaine buffer (0.2M $Na_2HPO_4$-0.1M citric acid, pH 6.2) and were suspended in the same buffer to make 5.0 ml. A 1.0 ml each portion of the suspension was put into 5 test tubes having an internal diameter of 15 mm. To the respective test tubes was added 1.0 ml of a solution or a suspension of (1) 25 mM L-tryptophan, (2) 25 mM L-phenylalanine, (3) 25 mM L-tyrosine, or (4) 25 mM L-DOPA (each containing 0.4 mM pyridoxal-5'-phosphate in McIlvaine buffer (pH 6.2)). Then, 2.0 ml of liquid paraffin was superimposed thereon and the suspension was allowed to stand at 30° C. for 1 hour to carry out the reaction. After completion of the reaction, the aqueous phase was taken out and was subjected to centrifugation to separate the supernatant. Amines produced in the supernatants corresponding to each amino acid were determined by HPLC. The results are shown in Table 5.

TABLE 5

| Substrates | Amine concentration (mM) | Relative activity (%) |
|---|---|---|
| L-tryptophan | 2.05 | 100 |
| L-phenylalanine | 2.48 | 121 |
| L-tyrosine | 0.96 | 47 |
| L-DOPA | 0.32 | 16 |

EXAMPLE 9
Purification of D-tryptophan

Fifty ml of the reaction mixture obtained in Example 3 was adjusted to pH 10 with 10% NaOH to completely dissolve tryptophan. The microbial cells were removed by centrifugation and the resulting supernatant was filtered through a ultrafiltration membrane (Amicon Co. YM-10) to remove high molecular weight substances such as protein. After adding 0.05 g of activated charcoal thereto, the filtrate was stirred for 1 hour under heating at 80° C. and then cooled to room temperature followed by filtration. The resulting filtrate was neutralized with acetic acid to pH 6.0 and deposited crystals of D-tryptophan were collected by filtration and dried. Recrystalization from water yielded 0.26 g white crystals. The purification yield was 50% and the chemical purity was 98.0%. Analysis by CROWNPAK CR(+) revealed that the optical purity of D-tryptophan was not less than 99% e.e.

EXAMPLE 10
Purification of tryptamine

Fifty ml of the reaction mixture obtained in Example 3 was centrifuged to remove microbial cells. The resulting supernatant was filtered through the ultrafiltration membrane (Amicon Co. YM-10) to remove high molecular weight substances such as protein. After adjusting pH to 10 with 10% NaOH, the filtrate was extracted three times 50 ml of toluene. After removal of the toluene phase and drying on anhydrous $Na_2SO_4$, the solvent was distilled off under reduced pressure to obtain 0.32 g of the residue. The purification yield was 77% and the chemical purity was 92.0%.

EXAMPLE 11
Purification of D-phenylalanine

Using the microbial cells prepared in Example 7, the reaction was conducted in the same manner as in Example 7 except for using 18 g of DL-phenylalanine as a substrate. After completion of the reaction, the reaction mixture was analyzed by HPLC and 10.9 g/l of phenethylamine and 14.5 g/l of phenylalanine were found to remain. The optical purity of D-phenylalanine was not less than 99% e.e. The yield of the substances was 49.5% and 48.3%, respectively.

EXAMPLE 12
Differences in activity between L-form and D-form substrates

A loopful of *Aspergillus oryzae* JCM 2059, *Aspergillus candidus* IFO 8816, *Pleurotus ostreatus* IFO 6515, and *Nectria flammea* IFO 30306 was each inoculated to 5 ml of the culture medium for preparation of microbial cells 1 and shake-cultured at 30° C. for 72 hours. To 4.0 ml of the culture taken out was added 0.2 ml of a 5% Tween 80 solution followed by incubation at 30° C. for 15 min. Live microbial cells obtained by centrifugation were washed twice with 100 mM Tris-HCl buffer (pH 8.0) and were suspended in the same buffer to make 2.0 ml. A 1.0 ml each portion of the suspension was placed into test tubes having an internal diameter of 15 mm and 1.0 ml of 1% L-tryptophan or 1% D-tryptophan/0.4 mM pyridoxal-5'-phosphate suspension (in 100 mM Tris-HCl buffer (pH 8.0)) was added thereto. Further, 2.0 ml of liquid paraffin was superimposed thereon and the suspension was allowed to stand at 30° C. for 17 hours to carry out the reaction. After completion of reaction, an aqueous phase taken out was centrifuged to obtain supernatant. The amount of produced tryptamine in the supernatant was determined by HPLC. The results are shown in Table 6.

TABLE 6

| Strain | Amount of tryptamine produced (mM) | | L-form/D-form activity ratio |
|---|---|---|---|
| | L-tryptophan | D-tryptophan | |
| *Aspergillus oryzae* JCM 2059 | 9.01 | 0.14 | 64.3 |
| *Aspergillus candidus* IFO 8816 | 3.66 | 0.05 | 73.2 |
| *Pleurotus ostreatus* IFO 6515 | 26.03 | 0.17 | 153.1 |
| *Nectria flammea* IFO 30306 | 16.33 | 0.22 | 74.2 |

What is claimed is:

1. A method of isolating a D-amino acid, the method comprising (A) contacting a mixture of enantiomers of an amino acid represented by formula (1-A) or formula (1-B)

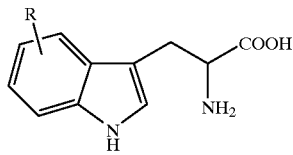

(1-A)

wherein R represents H or OH,

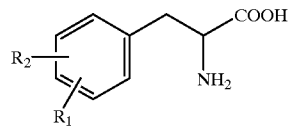

(1-B)

and each of $R_1$ and $R_2$ independently represents H or OH, with a microorganism that selectively degrades an L-amino acid of the amino acid represented by formula (1-A) or formula (1-B) to produce an amine represented by formula (2-A) or formula (2-B)

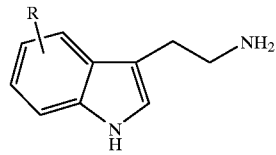

(2-A)

wherein R represents H or OH,

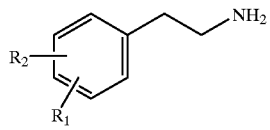

(2-B)

and each of $R_1$ and $R_2$ independently represents H or OH, and (B) recovering a D-amino acid from said mixture.

2. The method of claim 1, wherein said microorganism belongs to a genus selected from the group consisting of Fusarium, Gibberella, Aspergillus, Pleurotus, and Nectria.

3. The method of claim 2, wherein said microorganism belongs to a species selected from the group consisting of *Fusarium oxysporum, Fusarium solani, Gibberella fujikuroi, Aspergillus oryzae, Aspergillus candidus, Pleurotus ostreatus,* and *Nectria flammea.*

4. The method of claim 3, wherein said microorganism is selected from the group consisting of *Fusarium oxysporum* IFO 30705, *Fusarium oxysporum* IFO 31630, *Fusarium solani* IFO 9975, *Gibberella fujikuroi* IFO 9977, *Gibberella fujikuroi* IFO 30336, *Gibberella fujikuroi* IFO 30337, *Gibberella fujikuroi* IFO 31251, *Gibberella fujikuroi* NRIC 1240, *Aspergillus oryzae* IFO 5375, *Aspergillus oryzae* IFO 4265, *Aspergillus oryzae* JCM 2059, *Aspergillus candidus* IFO 4309, *Aspergillus candidus* IFO 8816, *Pleurotus ostreatus* IFO 6515, and *Nectria flammea* IFO 9628, and IFO 30306.

5. A method of producing an amine represented by formula (2-A) or formula (2-B), the method comprising contacting a mixture of enantiomers of an amino acid represented by formula (1-A) or formula (1-B), or an optically pure L-amino acid represented by formula (1-A) or (1-B), with a microorganism that selectively degrades an L-amino acid of the amino acid represented by formula (1-A) or formula (1-B), thereby producing an amine represented by formula (2-A) or (2-B).

6. The method of claim 5, wherein said microorganism belongs to a genus selected from the group consisting of Fusarium genus, Gibberella genus, Aspergillus genus, Pleurotus genus, and Nectria genus.

7. The method of claim 5, wherein said microorganism belongs to a species selected from the group consisting of *Fusarium oxysporum, Fusarium solani, Gibberella fujikuroi, Aspergillus oryzae, Aspergillus candidus, Pleurotus ostreatus* and *Nectria flammea.*

8. The method of claim 5, wherein said microorganism is selected from the group consisting of *Fusarium oxysporum* IFO 30705, *Fusarium oxysporum* IFO 31630, *Fusarium solani* IFO 9975, *Gibberella fujikuroi* IFO 9977, *Gibberella fujikuroi* IFO 30336, *Gibberella fujikuroi* IFO 30337, *Gibberella fujikuroi* IFO 31251, *Gibberella fujikuroi* NRIC 1240, *Aspergillus oryzae* IFO 5375, *Aspergillus oryzae* IFO 4265, *Aspergillus oryzae* JCM 2059, *Aspergillus candidus* IFO 4309, *Aspergillus candidus* IFO 8816, *Pleurotus ostreatus* IFO 6515, *Nectria flammea* IFO 9628, and *Nectria flammea* IFO 30306.

9. A method of isolating a D-amino acid, the method comprising (A) contacting a mixture of enantiomers of an amino acid represented by formula (1-A) or formula (1-B),

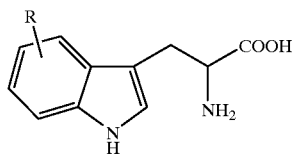

(1-A)

wherein R represents H or OH,

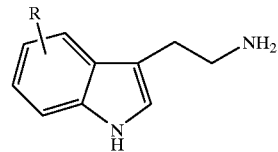

(1-B)

and each of $R_1$ and $R_2$ independently represents H or OH, with a treated product of a microorganism, wherein the treated product is selected from the group consisting of a lyophilized microorganism, an immobilized microorganism, a disrupted microorganism, a fraction of a lyophilized microorganism, and a fraction of a disrupted microorganism, and wherein the treated product selectively degrades an L-amino acid of the amino acid represented by formula (1-A) or formula (1-B) to produce an amine represented by formula (2-A) or formula (2-B),

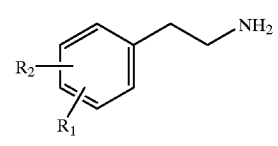

(2-A)

wherein R represents H or OH, (2-B)

and each of $R_1$ and $R_2$ independently represents H or OH; and (B) recovering a D-amino acid from said mixture.

10. The method of claim 9, wherein said microorganism belongs to a genus selected from the group consisting of Fusarium, Gibberella, Aspergillus, Pleurotus, and Nectria.

11. The method of in claim 10, wherein said microorganism belongs to a species selected from the group consisting of *Fusarium oxysporum, Fusarium solani, Gibberella fujikuroi, Aspergillus oryzae, Aspergillus candidus, Pleurotus ostreatus,* and *Nectria flammea.*

12. The method of claim 10, wherein said microorganism is selected from the group consisting of *Fusarium oxysporum* IFO 30705, *Fusarium oxysprorum* IFO 31630, *Fusarium solani* IFO 9975, *Gibberella fujikuroi* IFO 9977, *Gibberella fujikoni* IFO 30336, *Gibberella fujikoni* IFO 30337, *Gibberella fujikoni* IFO 31251, *Gibberella fujikoni* NRIC 1240, *Aspergillus oryzae* IFO 5375, *Aspergillus oryzae* IFO 4265, *Aspergillus oryzae* JCM 2059, *Aspergillus*

*candidus* IFO 4309, *Aspergillus candidus* IFO 8816, *Pleurotus ostreatus* IFO 6515, and *Nectria flammea* IFO 9628, and *Nectria flammea* IFO 30306.

13. A method of producing an amine represented by formula (2-A) or formula (2-B), the method comprising
contacting a mixture of enantiomers of an amino acid represented by formula (1-A) or formula (1-B), or an optically pure L-amino acid represented by formula (1-A) or (1-B), with a treated product of a microorganism, wherein the treated product is selected from the group consisting of a lyophilized microorganism, an immobilized microorganism, a disrupted microorganism, a fraction of a lyophilized microorganism, and a fraction of a disrupted microorganism, and wherein the treated product selectively degrades an L-amino acid of the amino acid represented by formula (1-A) or formula (1-B), thereby producing an amine represented by formula (2-A) or (2-B).

14. The method of claim 13, wherein said microorganism belongs to a genus selected from the group consisting of Fusarium genus, Gibberella genus, Aspergillus genus, Pleurotus genus, and Nectria genus.

15. The method of claim 14, wherein said microorganism belongs to a species selected from the group consisting of *Fusarium oxysporum, Fusarium solani, Gibberella fujikuroi, Aspergillus oryzae, Aspergillus candidus, Pleurotus ostreatus* and *Nectria flammea*.

16. The method of claim 15, wherein said microorganism is selected from the group consisting of *Fusarium oxysporum* IFO 30705, *Fusarium oxysporum* IFO 31630, *Fusarium solani* IFO 9975, *Gibberella fujikoroi* IFO 9977, *Gibberella fujikoroi* IFO 30336, *Gibberella fujikoroi* IFO 30337, *Gibberella fujikoroi* IFO 31251, *Gibberella fujikoroi* NRIC 1240, *Aspergillus oryzae* IFO 5375, *Aspergillus oryzae* IFO 4265, *Aspergillus oryzae* JCM 2059, *Aspergillus candidus* IFO 4309, *Aspergillus candidus* IFO 8816, *Pleurotus ostreatus* IFO 6515, *Nectria flammea* IFO 9628, and *Nectria flammea* IFO 30306.

* * * * *